(12) United States Patent
Braun et al.

(10) Patent No.: US 7,462,363 B2
(45) Date of Patent: Dec. 9, 2008

(54) INVERSE LATICES OF COPOLYMERS OF AMPS AND OF N,N-DIMETHYLACRYLAMIDE; COSMETIC USE

(75) Inventors: Olivier Braun, Castres (FR); Paul Mallo, Croissy-sur-Seine (FR); Stephanie Basset, Castres (FR)

(73) Assignee: Societe d'Exploitation de Produits pour les Industries Chimiques Seppic, Paris (FR)

( * ) Notice: Subject to any disclaimer, the term of this patent is extended or adjusted under 35 U.S.C. 154(b) by 0 days.

(21) Appl. No.: 11/439,208

(22) Filed: May 24, 2006

(65) Prior Publication Data
US 2006/0269490 A1 Nov. 30, 2006

(30) Foreign Application Priority Data
May 25, 2005 (FR) ................... 05 51370

(51) Int. Cl.
A61K 8/02 (2006.01)
A61Q 17/04 (2006.01)

(52) U.S. Cl. ........................... 424/401; 424/59

(58) Field of Classification Search .......... 424/401, 424/59; 514/938, 937
See application file for complete search history.

(56) References Cited

U.S. PATENT DOCUMENTS 4,254,249 A    3/1981  Cottrell et al.
6,197,287 B1 * 3/2001  Mallo et al. ............. 424/70.16
6,414,080 B1 * 7/2002  Loeffler et al. ............. 524/801

FOREIGN PATENT DOCUMENTS

| EP | 0 503 853   | * | 9/1992 |
| EP | 0 887 362 A1 |   | 12/1998 |
| FR | 2 774 688   |   | 8/1999 |
| FR | 2 861 397 A1 |   | 4/2005 |
| FR | 2 873 126   |   | 1/2006 |
| FR | 2 874 617   |   | 3/2006 |
| GB | 960331      |   | 6/1964 |
| WO | WO 99/36445 |   | 7/1999 |
| WO | WO 01/35922 A1 |   | 8/2001 |

OTHER PUBLICATIONS

Normant et al., "Chimie Organique", Cours de Chimis. 1968, pp. 355-357.
March, "Advanced Organic Chemistry", John Wiley & Sons, 1985, pp. 983-984.

* cited by examiner

*Primary Examiner*—Johann Richter
*Assistant Examiner*—Konata M. George
(74) *Attorney, Agent, or Firm*—Young & Thompson

(57) ABSTRACT

Composition including an oil phase, an aqueous phase, at least one emulsifying system of water-in-oil (W/O) type, optionally at least one emulsifying system of oil-in-water (O/W) type, in the form of an inverse latex including from 20% to 70% by mass and preferably from 25% to 50% by mass of a branched or crosslinked polyelectrolyte, characterized in that the polyelectrolyte is a copolymer of 2-acrylamido-2-methylpropanesulfonic acid partially or totally salified with N,N-dimethylacrylamide and optionally one or more monomers chosen from monomers containing a partially or totally salified weak acid function and neutral monomers. Cosmetic use.

11 Claims, 1 Drawing Sheet

| Mass concentrations of Triglyceride 5545 in the cream-gel prepared with Composition 5 ||||| 
|---|---|---|---|---|
| 30% | 35% | 40% | 45% | 50% |
| Appearance of the cream-gel after 7 days, observed under a microscope at a magnification of × 400 |||||

| Mass concentrations of Triglyceride 5545 in the cream-gel prepared with Composition 5 ||||
|---|---|---|---|
| 55% | 60% | 65% | 70% |
| Appearance of the cream-gel after 7 days, observed under a microscope at a magnification of × 400 ||||

| Mass concentrations of Triglyceride 5545 in the cream-gel prepared with Composition 5 ||||||
|---|---|---|---|---|---|
| 30% | 35% | 40% | 45% | 50% ||
| Appearance of the cream-gel after 7 days, observed under a microscope at a magnification of × 400 ||||||
|  | 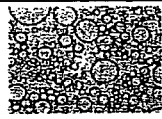 | 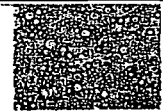 | 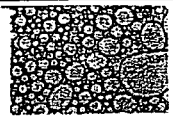 |  ||

| Mass concentrations of Triglyceride 5545 in the cream-gel prepared with Composition 5 ||||
|---|---|---|---|
| 55% | 60% | 65% | 70% |
| Appearance of the cream-gel after 7 days, observed under a microscope at a magnification of × 400 ||||
|  |  | 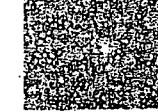 | 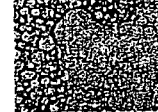 |

Figure 1

| Mass concentrations of Primol™ 352 in the cream-gel prepared with Composition 5 |||||
|---|---|---|---|---|
| 30% | 40% | 50% | 60% | 70% |
| Appearance of the cream-gel after 7 days, observed under a microscope at a magnification of × 400 |||||
|  |  | 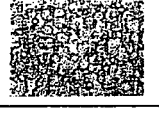 | 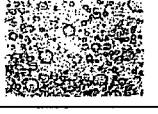 |  |

Figure 2

| Mass concentrations of Triglyceride 5545 in the cream-gel prepared with Composition a ||
|---|---|
| 40% | 45% |
| Appearance of the cream-gel after 7 days, observed under a microscope at a magnification of × 400 ||
|  | 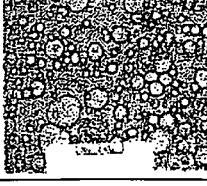 |

Figure 3

INVERSE LATICES OF COPOLYMERS OF AMPS AND OF N,N-DIMETHYLACRYLAMIDE; COSMETIC USE

The present patent application relates to water-in-oil inverse latex, to a process for preparing them and to their use as thickeners and/or emulsifiers for skincare and haircare products or for the manufacture of cosmetic, dermocosmetic, dermopharmaceutical or pharmaceutical preparations.

The thickeners used in the cosmetics or pharmaceutical industry, are intended to thicken aqueous phases, lotions or cream-gels. In the case of cream-gels, an emulsifier is also added, especially when it is desired to incorporate a high content of oil into the formulation. However, emulsifiers are often products with a low molecular weight, which are potentially less tolerated by the skin than polymers. Furthermore, the use of polymers allows the preparation of cream-gels without heating, which reduces the manufacturing costs while at the same time keeping the heat-sensitive molecules intact.

Accordingly, it has been sought to develop polymers that are both thickeners and emulsifiers. Synthetic thickening polymers in the form of inverse latex are nowadays frequently used, for instance those described in the French patent applications published under the numbers 2 721 511, 2 733 805, 2 774 688, 2 774 996 and 2 782 086 and also in the European patent application published under the number EP 0 503 853.

Japanese patent 3 681 154 discloses a cosmetic preparation formulated with a copolymer obtained copolymerization of 2-acrylamide-2-methyl propanesulfonic acid or a salt, a dialkyl acrylamide and a crosslinking monomer. However this copolymer is not an inverse latex.

U.S. patent application published under number U.S. 2004/0062728 A1, discloses a cosmetic composition comprising an amphiphilic polymer comprising 2-acrylamido-2-methyl-propanesulfonic acid monomer in free or partially or totally neutralized forms and at least one hydrophobic portion of the type (C8 to C16 alkyl) acrylamide.

European patent application published under number EP 1 59 305, discloses an inverse emulsion polymer composition comprising a copolymer or copolymer salt of N,N-dimethylacrylamide and 2-acrylamido-2-methylpropane sulfonic acid or acid salts, thereof, having a brookfield viscosity of less than 20.000 Cps at 25° C., a polymer reduced viscosity at 0.0005 g/cm$^3$ (0.05 gm/dl) active in one Normal (1N) NaCl at 30° C., of about 3.10$^3$ cm$^3$/g to about 10$^4$ cm$^3$/g (30 to about 10 dl/g). This low polymer reduced viscosity is generated by the presence of a chain transfer agent during the process of manufacturing, such as isopropanol or 2-mercapto ethanol. It is also induced either by the absence of crosslinking agent or by the presence of only a small quantity crosslinking agent. However, such a low reduced viscosity is characteristic of a low molar mass of the polymer, which prevents it from having an efficient thickening power.

In the context of its research to develop novel emulsifying and thickening compounds, the Applicant became interested in novel 2-acrylamido-2-methylpropanesulfonic acid polymers.

One subject of the invention is thus a composition comprising an oil phase, an aqueous phase, at least one emulsifying system of water-in-oil (W/O) type, optionally at least one emulsifying system of oil-in-water (O/W) type, in the form of an inverse latex comprising from 20% to 70% by mass and preferably from 25% to 50% by mass of a branched or crosslinked polyelectrolyte, characterized in that the said polyelectrolyte is a copolymer of 2-acrylamido-2-methylpropanesulfonic acid partially or totally salified with N,N-dimethylacrylamide and optionally one or more monomers chosen from monomers containing a partially or totally salified weak acid function and/or from neutral monomers other than N,N-dimethylacrylamide.

In the composition as defined above, the said polyelectrolyte has a polymer reduced viscosity at 0.0005 g/cm$^3$ (0.05 gm/dl) active in one Normal (1N) NaCl at 30° C., greater than 10$^4$ cm$^3$/g (10 dl/g), and more particularly greater than 1.5 10$^4$ cm$^3$/g (15 dl/g).

In the composition as defined above, 2-methyl-2-[(1-oxo-2-propenyl)amino]-1-propanesulfonic acid is preferably partially or totally salified in the form of an alkali metal salt, for example the sodium salt or the potassium salt, the ammonium salt, an amino alcohol salt, for instance the monoethanolamine salt, or an amino acid salt, for instance the lysine salt.

The weak acid function of the monomers comprising one is especially a partially salified carboxylic acid function. The said monomers may be, for example, partially or totally salified acrylic acid, methacrylic acid, itaconic acid, maleic acid or 3-methyl-3-[(1-oxo-2-propenyl)amino]butanoic acid. They are preferably partially or totally salified in the form of an alkali metal salt, for instance the sodium salt or the potassium salt, the ammonium salt, an amino alcohol salt, for instance the monoethanolamine salt, or an amino acid salt, for instance the lysine salt.

The neutral monomers other than N,N-dimethylacrylamide are especially chosen from acrylamide, methacrylamide, diacetoneacrylamide, N-isopropylacrylamide, N-[2-hydroxy-1,1-bis[(hydroxymethyl)ethyl]]propenamide [or tris(hydroxymethyl)acrylamidomethane or N-tris(hydroxymethyl)methylacrylamide also known as THAM], (2-hydroxyethyl)acrylate, (2,3-dihydroxypropyl)acrylate, (2-hydroxyethyl)methacrylate, (2,3-dihydroxypropyl)methacrylate, an ethoxylated derivative with a molecular weight of between 400 and 1000, of each of these esters, or vinylpyrrolidone.

The polyelectrolyte present in the composition as defined above comprises between 95 mol % and 25 mol % of partially or totally salified 2-methyl-2-[(1-oxo-2-propenyl)amino]-1-propanesulfonic acid monomer and between 5 mol % and 75 mol % of N,N-dimethylacrylamide monomer.

According to one particular aspect of the present invention, the polyelectrolyte present in the composition comprises between 90 mol % and 40 mol % of partially or totally salified 2-methyl-2-[(1-oxo-2-propenyl)amino]-1-propanesulfonic acid monomer and between 10 mol % and 60 mol % of N,N-dimethylacrylamide monomer.

When the polyelectrolyte present in the composition as defined above is a copolymer of partially or totally salified 2-acrylamido-2-methylpropanesulfonic acid, of N,N-dimethylacrylamide and of one or more monomers chosen from monomers containing a weak acid function and/or neutral monomers other than N,N-dimethylacrylamide, the mole proportion of all of the monomers chosen from the monomers containing a weak acid function and the neutral monomers other than N,N-dimethylacrylamide is greater than 0% and less than or equal to 30%.

In the first case, the mole ratio between the N,N-dimethylacrylamide and all of the monomers chosen from the monomers containing a weak acid function and the neutral monomers other than N,N-dimethylacrylamide is preferably greater than or equal to 1.

The term "branched polymer" denotes a non-linear polymer containing side chains so as to obtain, when this polymer is dissolved in water, extensive entanglement leading to very high viscosities at low shear.

The term "crosslinked polymer" denotes a non-linear polymer in the form of a water-insoluble but water-swellable three-dimensional network thus leading to the production of a chemical gel.

The composition according to the invention may comprise crosslinked units and/or branched units.

When the polymer present in the composition that is the subject of the present invention is crosslinked, it is more particularly crosslinked with a diethylenic or polyethylenic compound in a mole proportion, expressed relative to the monomers used, of from 0.005% to 1%, more particularly from 0.010% to 0.20% and still more particularly from 0.015% to 0.15%. Preferably, the crosslinking agent and/or the branching agent is chosen from ethylene glycol dimethacrylate, diethylene glycol diacrylate, sodium diallyloxyacetate, ethylene glycol diacrylate, diallylurea, triallylamine, trimethylolpropane triacrylate and methylenebis (acrylamide).

In the composition as defined above, the emulsifying system of water-in-oil (W/O) type consists either of a sole surfactant or of a mixture of surfactants on condition that the HLB value of the said mixture is low enough to induce water-in-oil emulsions. As emulsifiers of water-in-oil type, there are, for example, sorbitan esters, for instance sorbitan oleate, for instance the product sold by the company SEPPIC under the name Montane™ 80, sorbitan isostearate, for instance the product sold by the company SEPPIC under the name Montane™ 70, or sorbitan sesquioleate, for instance the product sold by the company SEPPIC under the name Montane™ 83. There are also certain polyethoxylated sorbitan esters, for example pentaethoxylated sorbitan monooleate, for instance the product sold by the company SEPPIC under the name Montanox™ 81 or pentaethoxylated sorbitan isostearate, for instance the product sold under the name Montanox™ 71 by the company SEPPIC. There is also diethoxylated oleocetyl alcohol, for instance the product sold under the name Simulsol™ OC 72 by the company SEPPIC, tetraethoxylated lauryl acrylate, for instance the product sold under the name Blemmer™ ALE 200 or polyesters with a molecular weight of between 1000 and 3000, produced from condensation between a poly(isobutenyl)succinic acid or its anhydride and polyethylene glycol, such as Hypermer™ 2296 sold by the company Uniqema, or, finally, block copolymers with a molecular weight of between 2500 and 3500, for instance Hypermer™ B246 sold by the company Uniqema or Simaline™ IE 200 sold by the company SEPPIC.

The composition that is the subject of the present invention generally comprises from 2% to 8% by mass of emulsifying system of water-in-oil (W/O) type.

When the composition as defined above comprises an emulsifying system of oil-in-water (O/W) type, it consists either of a sole surfactant or of a mixture of surfactants, on condition that the HLB value of the said mixture is high enough to induce oil-in-water emulsions. As emulsifiers of oil-in-water type, there are, for example, ethoxylated sorbitan esters, for instance sorbitan oleate polyethoxylated with 20 mol of ethylene oxide, sold by the company SEPPIC under the name Montanox™ 80, sorbitan laurate polyethoxylated with 20 mol of ethylene oxide, sold by the company SEPPIC under the name Montanox™ 20, castor oil polyethoxylated with 40 mol of ethylene oxide, sold under the name Simulsol™ OL50, decaethoxylated oleodecyl alcohol, sold by the company SEPPIC under the name Simulsol™ OC710, heptaethoxylated lauryl alcohol, sold under the name Simulsol™ P7 or sorbitan monostearate polyethoxylated with 20 mol of ethylene oxide, sold by the company SEPPIC under the name Montanox™ 60.

When the composition that is the subject of the present invention comprises an emulsifying system of oil-in-water (O/W) type, it generally comprises from 3% to 8% by mass of this system.

According to one particular aspect of the present invention, the composition as defined above comprises an (O/W) emulsifying system.

In the composition that is the subject of the present invention, the oil phase comprises a commercial mineral oil containing saturated hydrocarbons, for instance paraffins, isoparaffins or cycloparaffins, having at room temperature a density of between 0.7 and 0.9 and a boiling point of greater than about 250° C., for instance Marcol™ 52, Isopar™ M or Isopar™ L sold by Exxon Chemical; isohexadecane, identified in Chemical Abstracts by the number RN=93685-80-4, which is a mixture of $C_{12}$, $C_{16}$ and $C_{20}$ isoparaffins containing at least 97% of $C_{16}$ isoparaffins, among which the main constituent is 2,2,4,4,6,8,8-heptamethylnonane (RN=4390-04-9); it is sold in France by the company Bayer, or isododecane also sold in France by the company Bayer; or a synthetic oil such as hydrogenated polydecene or hydrogenated polyisobutene, sold in France by the company Ets B. Rossow et Cie under the name Parleam-Polysynlane™. It is cited in: Michel and Irene Ash; Thesaurus of Chemical Products, Chemical Publishing Co. Inc. 1986 Volume I, page 211 (ISBN 0 7131 3603 0); or a plant oil, for instance squalane of plant origin sold in France by the company Sophim, under the name Phytosqualane™ and identified in Chemical Abstracts by the number RN=111-01-3; it is a mixture of hydrocarbons containing more than 80% by weight of 2,6,10,15,19,23-hexamethyltetracosane, or of a mixture of several of these oils.

The oil phase may also comprise fatty acid esters.

In the context of the present invention, the term "fatty acid ester" means a compound of formula (I):

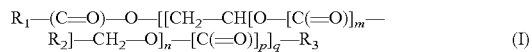

$$R_1-(C=O)-O-[[CH_2-CH[O-[C(=O)]_m-R_2]-CH_2-O]_n-[C(=O)]_p]_q-R_3 \qquad (I)$$

in which:

$R_1$ represents a saturated or unsaturated, linear or branched hydrocarbon-based chain containing from 7 to 30 carbon atoms, $R_2$ represents, independently of $R_1$, a hydrogen atom or a saturated or unsaturated, linear or branched hydrocarbon-based chain containing from 7 to 30 carbon atoms, $R_3$ represents, independently of $R_1$ or $R_2$, a hydrogen atom or a saturated or unsaturated, linear or branched hydrocarbon-based chain containing from 1 to 30 carbon atoms, m, n, p and q are, independently of each other, equal to 0 or 1, it being understood that when $R_3$ represents a hydrogen atom, q is other than 0.

In formula (I) as defined above, $R_1$, $R_2$ and $R_3$ especially represent, independently of each other, a radical chosen from heptyl, octyl, nonyl, decyl, undecyl, dodecyl, tridecyl, tetradecyl, pentadecyl, hexadecyl, heptadecyl, octadecyl, nonadecyl, eicosyl, uneicosyl, docosyl, heptadecenyl, eicosenyl, uneicosenyl, docosenyl, heptadecadienyl and decenyl radicals; the group $R_1$—C(=O)— more particularly represents one of the following radicals: octanoyl(caprylyl), decanoyl, undecylenoyl, dodecanoyl(lauroyl), tetradecanoyl(myristyl), hexadecanoyl(palmitoyl), octadecanoyl(stearyl), eicosanoyl (arachidoyl), docosanoyl(behenoyl), 8-octadecenoyl(oleyl), eicosenoyl(gadoloyl), 13-docosenoyl(erucyl), 9,12-octadecadienoyl(linoleoyl), 9,12,15-octadecatrienoyl(linolenoyl).

The oil phase may more particularly comprise a compound of formula (Ia):

$$R_1-(C=O)-O-CH_2-CH[O-[C(=O)]_m-R_2]-CH_2-O-[C(=O)]_p-R_3 \quad (Ia)$$

corresponding to formula (I) as defined above in which q and n are equal to 1, or a mixture of compounds of formula (Ia). In this case, it is preferably either a compound of formula (Ia$_1$):

$$R_1-(C=O)-O-CH_2-CH(OH)-CH_2-OH \quad (Ia_1)$$

corresponding to formula (Ia) as defined above in which m and p are equal to 0 and $R_2$ and $R_3$ represent a hydrogen atom, or a compound of formula (Ia$_2$)

$$R_1-(C=O)-O-CH_2-CH(OH)-CH_2-O-C(=O)-R_3 \quad (Ia_2)$$

corresponding to formula (Ia) as defined above in which p is equal to 1, m is equal to 0 and $R_2$ represents a hydrogen atom, or a compound of formula (Ia$_3$)

$$R_1-(C=O)-O-CH_2-CH[O-C(=O)-R_2]-CH_2-O-C(=O)-R_3 \quad (Ia_3)$$

corresponding to formula (Ia) as defined above in which m and p are equal to 1, or a mixture of compounds of formulae (Ia$_1$), (Ia$_2$) and/or (Ia$_3$).

As examples of compounds of formula (Ia$_1$), (Ia$_2$) or (Ia$_3$), there are, for example, fatty acid triglycerides or fatty acid mixtures such as the mixture of fatty acid triglycerides containing from 6 to 10 carbon atoms, sold under the name Softenol™ 3819, the mixture of fatty acid triglycerides containing from 8 to 10 carbon atoms, sold under the name Softenol™ 3108, the mixture of fatty acid triglycerides containing from 8 to 18 carbon atoms, sold under the name Softenol™ 3178, the mixture of fatty acid triglycerides containing from 12 to 18 carbon atoms, sold under the name Softenol™ 3100, the mixture of fatty acid triglycerides containing 7 carbon atoms, sold under the name Softenol™ 3107, the mixture of fatty acid triglycerides containing 14 carbon atoms, sold under the name Softenol™ 3114, or the mixture of fatty acid triglycerides containing 18 carbon atoms, sold under the name Softenol™ 3118, glyceryl dilaurate, glyceryl dioleate, glyceryl isostearate, glyceryl distearate, glyceryl monolaurate, glyceryl monooleate, glyceryl monoisostearate or glyceryl monostearate, or a mixture of these compounds.

The oil phase may more particularly comprise a compound of formula (Ib):

$$R_1-(C=O)-O-R_3 \quad (Ib)$$

corresponding to formula (I) as defined above in which q is equal to 0, or a mixture of compounds of formula (Ib).

An example of a compound of formula (Ib) is, for example, octyl palmitate.

The inverse latex as defined above generally contains from 4% to 10% by weight of emulsifiers.

Its oil phase represents from 15% to 40% and preferably from 20% to 25% of the total weight of the composition.

The aqueous phase represents from 2% to 40% of the total weight of the composition.

According to another particular aspect of the present invention, a subject thereof is a composition as defined above in which the copolymer is chosen from:
crosslinked copolymers of 2-methyl-2-[(1-oxo-2-propenyl)amino]-1-propanesulfonic acid partially salified in the form of the sodium salt and of N,N-dimethylacrylamide;
crosslinked copolymers of 2-methyl-2-[(1-oxo-2-propenyl)amino]-1-propanesulfonic acid partially salified in the form of the ammonium salt and of N,N-dimethylacrylamide;
crosslinked copolymers of 2-methyl-2-[(1-oxo-2-propenyl)amino]-1-propanesulfonic acid partially salified in the form of the potassium salt and of N,N-dimethylacrylamide;
crosslinked terpolymers of 2-methyl-2-[(1-oxo-2-propenyl)amino]-1-propanesulfonic acid partially salified in the form of the sodium salt, of the potassium salt or of the ammonium salt, of acrylic acid partially salified in the form of the sodium salt, the potassium salt or the ammonium salt and of N,N-dimethylacrylamide;
crosslinked tetrapolymers of 2-methyl-2-[(1-oxo-2-propenyl)amino]-1-propanesulfonic acid partially salified in the form of the sodium salt, the potassium salt or the ammonium salt, of acrylic acid partially salified in the form of the sodium salt, the potassium salt or the ammonium salt, of N,N-dimethylacrylamide and of acrylamide;
crosslinked terpolymers of 2-methyl-2-[(1-oxo-2-propenyl)amino]-1-propanesulfonic acid partially salified in the form of the sodium salt, the potassium salt or the ammonium salt, of N,N-dimethylacrylamide and of acrylamide;
crosslinked terpolymers of 2-methyl-2-[(1-oxo-2-propenyl)amino]-1-propanesulfonic acid partially salified in the form of the sodium salt, the potassium salt or the ammonium salt, of N,N-dimethylacrylamide and of N-isopropylacrylamide;
crosslinked terpolymers of 2-methyl-2-[(1-oxo-2-propenyl)amino]-1-propanesulfonic acid partially salified in the form of the sodium salt, the potassium salt or the ammonium salt, of N,N-dimethylacrylamide and of N-[2-hydroxy-1,1-bis(hydroxymethyl)ethyl]propenamide;
crosslinked tetrapolymers of 2-methyl-2-[(1-oxo-2-propenyl)amino]-1-propanesulfonic acid partially salified in the form of the sodium salt, the potassium salt or the ammonium salt, of acrylic acid partially salified in the form of the sodium salt, the potassium salt or the ammonium salt, of N,N-dimethylacrylamide and of (2-hydroxyethyl)acrylate;
crosslinked terpolymers of 2-methyl-2-[(1-oxo-2-propenyl)amino]-1-propanesulfonic acid partially salified in the form of the sodium salt, the potassium salt or the ammonium salt, of N,N-dimethylacrylamide and of (2-hydroxyethyl)acrylate.

According to another particular aspect of the present invention, the composition as defined above comprises at least 50% by weight and not more than 70% by weight of polyelectrolyte. In this case, the composition is preferably prepared by performing the following process:

a) an aqueous phase containing the monomers and the possible hydrophilic additives is emulsified in an organic phase containing the surfactant system of water-in-oil (W/O), type, a mixture consisting of the oil intended to be present in the final composition and of a volatile oil, and the possible hydrophobic additives, b) the polymerization reaction is initiated by introducing a free-radical initiator into the emulsion formed in a), and the reaction is then allowed to proceed, and c) the reaction medium from step b) is concentrated by distillation until the said volatile oil has been completely removed.

The volatile oils that are suitable for performing the process as defined above are, for example, light isoparaffins containing from 8 to 11 carbon atoms, for instance those sold under the names Isopar™ G, Isopar™ L, Isopar™ H or Isopar™ J.

According to one preferred embodiment of the process as defined above, the polymerization reaction is initiated with a redox couple, such as the cumene hydroperoxide/sodium metabisulfite couple, at a temperature of less than or equal to 10° C., and is then performed either quasi-adiabatically up to a temperature of greater than or equal to 40° C. and more particularly greater than or equal to 50° C., or by controlling the change of the temperature.

When step c) is complete, the emulsifying system of oil-in-water type is introduced, if desired, at a temperature below 50° C.

When the composition as defined above comprises less than 50% by weight of polyelectrolyte, it is preferably prepared by performing the following process:
  a) an aqueous phase containing the monomers and the possible additives is emulsified in an oil phase in the presence of one or more emulsifiers of water-in-oil type,
  b) the polymerization reaction is initiated by introducing a free-radical initiator into the emulsion formed in a), and the reaction is then allowed to proceed,
  c) when the polymerization reaction is complete, one or more emulsifiers of oil-in-water type are introduced, if desired, at a temperature below 50° C.

According to one variant of this process, the reaction medium obtained form step b) is concentrated by distillation before performing step c).

According to one preferred embodiment of the process as defined above, the polymerization reaction is initiated with a redox couple, such as the cumene hydroperoxide/sodium metabisulfite couple, at a temperature of less than or equal to 10° C., and is then performed either quasi-adiabatically up to a temperature of greater than or equal to 40° C. and more particularly greater than or equal to 50° C., or by controlling the change of the temperature.

According to another preferred embodiment of the process, the aqueous starting solution is adjusted to a pH of less than or equal to 4 before performing step a).

According to another particular aspect of the present invention, the composition as defined above comprises not more than 30% by weight of polyelectrolyte.

A subject of the invention is also a cosmetic, dermopharmaceutical or pharmaceutical composition, characterized in that it comprises as thickening and/or emulsifying compound at least one inverse latex as defined above.

The cosmetic, dermocosmetic, dermopharmaceutical or pharmaceutical composition defined above generally comprises from 0.1% to 10% and more particularly between 0.5% and 5% by weight of the said inverse latex. It is especially in the form of a milk, a lotion, a gel, a cream-gel, a cream, a soap, a bubblebath, a balm, a shampoo or a conditioner.

According to one preferred aspect of the present invention, the cosmetic, dermocosmetic, dermopharmaceutical or pharmaceutical composition as defined above is a topical composition.

A subject of the invention is also the use of the inverse latex as defined above for proposing a cosmetic, dermopharmaceutical or pharmaceutical topical composition.

The topical composition according to the invention, intended to be applied to the skin or mucous membranes of man or animals, may consist of a topical emulsion comprising at least one aqueous phase and at least one oil phase. This topical emulsion may be of the oil-in-water type. More particularly, this topical emulsion may consist of a fluid emulsion, such as a milk or a fluid gel. The oil phase of the topical emulsion may consist of a mixture of one or more oils.

A topical composition according to the invention may be intended for cosmetic use or may be used to prepare a medicament for treating skin and mucous membrane diseases. In the latter case, the topical composition then comprises an active principle that may consist, for example, of an anti-inflammatory agent, a muscle relaxant, an antifungal agent or an antibacterial agent.

The compositions according to the invention may also contain ingredients usually used in the cosmetic and dermopharmaceutical fields and known to those skilled in the art, such as fats (oils, butters, waxes, fatty acids and gums), emulsifiers and coemulsifiers, gelling agents and/or stabilizers and/or film-forming agents, fillers, pigments, sunscreens, humectants, solvents and cosolvents, plasticizers, sequestrants, antioxidants, fragrances, preserving agents or active principles. As examples of oils that may be combined with the composition of the invention, mention may be made of paraffins, isoparaffins, white mineral oils, plant oils, animal oils, synthetic oils, silicone oils and fluoro oils; and more particularly:

oils of plant origin, such as sweet almond oil, coconut oil, castor oil, jojoba oil, olive oil, rapeseed oil, groundnut oil, sunflower oil, wheatgerm oil, corn germ oil, soybean oil, cottonseed oil, alfalfa oil, poppyseed oil, pumpkin oil, evening primrose oil, millet oil, barley oil, rye oil, safflower oil, candlenut oil, passionflower oil, hazelnut oil, palm oil, shea butter, apricot kernel oil, beauty-leaf oil, sysymbrium oil, avocado oil, calendula oil and floral or legume oils; ethoxylated plant oils; oils of animal origin, such as squalene and squalane; mineral oils, such as liquid paraffin, liquid petroleum jelly and isoparaffins; synthetic oils, especially fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate or isocetyl lanolate, fatty acid monoglycerides, diglycerides and triglycerides, for instance glyceryl triheptanoate, alkylbenzoates, poly-α-olefins, polyolefins, for instance polyisobutene, synthetic isoalkanes, for instance isohexadecane, isododecane, perfluoro oils and silicone oils. Among the silicone oils, mention may be made more particularly of dimethylpolysiloxanes, methylphenylpolysiloxanes, silicones modified with amines, silicones modified with fatty acids, silicones modified with alcohols, silicones modified with alcohols and fatty acids, silicones modified with polyether groups, epoxy-modified silicones, silicones modified with fluoro groups, cyclic silicones and silicones modified with alkyl groups.

As another fatty substance that may be combined with the composition of the invention, mention may be made of fatty alcohols or fatty acids.

The fatty phase of the preparations according to the invention may also contain waxes such as beeswax; carnauba wax; candelilla wax, ouricury wax; japan wax;, cork fibre wax or sugarcane wax; paraffin waxes; lignite waxes; microcrystalline waxes; lanolin wax; ozokerite; polyethylene wax; hydrogenated oils; silicone waxes; plant waxes; fatty alcohols and fatty acids that are solid at room temperature; glycerides that are solid at room temperature.

The inverse latex according to the invention may optionally be combined with other thickening and/or emulsifying polymers. Examples that may be mentioned include homopolymers or copolymers of acrylic acid or of acrylic acid derivatives, homopolymers or copolymers of acrylamide, homopolymers or copolymers of acrylamide derivatives, homopolymers or copolymers of acrylamido-methylpropanesulfonic acid, of vinyl monomer, of trimethylaminoethyl acrylate chloride sold under the names Carbopol™ Ultrez™ 10, Pemulen™ TR1, Pemulen™ TR2, Simulgel™ A, Simulgel™ NS, Simulgel™ EPG, Simulgel™ EG, Luvigel™ EM, Salcare™ SC91, Salcare™ SC92, Salcare™ SC95, Salcare™ SC96, Flocare™ ET100, Hispagel™, Sepigel™ 305, Sepigel™ 501, Sepigel™ 502, Sepiplus, Flocare™ ET58 and Stabileze™ 06; hydro-colloids of plant or biosynthetic origin, for instance xanthan gum, karaya gum, carrageenates or alginates; silicates; cellulose and its derivatives; starch and its hydrophilic derivatives; polyurethanes.

The composition according to the invention is also an advantageous substitute for those sold under the names Sepigel™ 305, Sepigel™ 501, Simulgel™ EG, Simulgel™ NS or Simulgel™ 600 by the Applicant, since it also shows good compatibility with the other excipients used for the preparation of formulations such as milks, lotions, creams, creamgels, soaps, bubblebaths, balms, shampoos or hair conditioners.

It is especially compatible with the concentrates described and claimed in the international publications WO 92/06778, WO 95/04592, WO 95/13863, WO 96/37285, WO 98/22207, and WO 98/47610 or in FR 2 734 496, with the surfactants described in WO 93/08204.

Among the emulsifiers that may be used in the presence of the inverse latex according to the invention, examples that may be mentioned include fatty acids; ethoxylated fatty acids; fatty acid esters of sorbitol; ethoxylated fatty acid esters; polysorbates; polyglycerol esters; ethoxylated fatty alcohols; sucrose esters; alkylpolyglycosides; sulfated or phosphated fatty alcohols or mixtures of alkylpoly-glycosides and of fatty alcohols described in French patent applications 2 668 080, 2 734 496, 2 756 195, 2 762 317, 2 784 680, 2 784 904, 2 791 565, 2 790 977, 2 807 435 and 2 804 432, Sensanov and Fluidanov.

The cosmetic, dermocosmetic, dermopharmaceutical or pharmaceutical composition as defined above may also comprise texture agents and/or fillers, for instance acrylic and methacrylic acid copolymers, starches, silicas, calcium, magnesium, aluminium or barium silicates, calcium phosphate, natural fibres such as cotton fibre, cellulose fibre or chitosan fibre, or synthetic fibres such as polyamide (Nylon®) fibre, rayon fibre, viscose fibre, cellulose acetate fibre, poly-p-phenyleneterephthamide fibre (Kevlar®), polyethylene or polypropylene fibre, glass fibre, carbon fibre, Teflon fibre, polyester fibre, polyvinyl chloride fibre, polyvinyl alcohol fibre, polyacrylonitrile fibre, polyurethane fibre or polyethylene phthalate fibre, talc, mica, sericite, silica, boron nitride, lauroyllysine, silicone resin powders, calcium carbonate, magnesium carbonate, titanium oxide, zinc oxide or cerium oxide, titanium micas, iron oxides and other mineral or organic pigments, or a mixture of these powders.

As examples of active principles that may be combined with the inverse latex according to the invention, mention may be made of compounds with a lightening or depigmenting action, a moisturizing action, a tensioning action, a calmative or relaxing action, a purifying, seboregulatory or hair-loss-countering action, an anti-ageing action, or a firming, restructuring action, a free-radical-scavenging action, an antioxidant action or a self-tanning action. The composition of the invention may thus be combined with active agents such as, for example, arbutin, kojic acid, hydroquinone, ellagic acid, vitamin C and its derivatives, Stay C, magnesium ascorbyl phosphate and its derivatives, ascorbyl glucoside, phytic acid, fruit acids, rucinol or resorcinol, azeleic acid, dihydroxyacetone (DHA), lipoic acid, Vegewhite™, Gatuline™, Synerlight™, Biowhite™, Phytolight™, Dermalight™, Clariskin™, Melaslow™, Dermawhite™, Ethioline™, Melarest™, Gigawhite™, Albatine™, Lumiskin™, polyphenol extracts, grape extracts, pine extracts, wine extracts, olive extracts, tea extracts, cocoa extracts, Amazonian forest plant extracts, legume extracts, floral extracts, fruit extracts, mint extracts, pond extracts, N-acyl proteins, N-acyl peptides, for instance Matrixyl™, N-acylamino acids, partial hydrolysates of N-acyl proteins, amino acids, peptides, total protein hydrolysates, partial protein hydrolysates, polyols (for instance glycerol, butylene glycol, etc.), milk derivatives, Aquaxyl™, urea, pyrrolidonecarboxylic acid or derivatives of this acid, glycyrrhetinic acid or its derivatives, α-bisabolol, sugars or sugar derivatives, polysaccharides or derivatives thereof, hydroxy acids, for instance lactic acid or salicylic acid, vitamins, vitamin derivatives, for instance retinol, retinol derivatives, vitamin E and its derivatives, minerals, trace elements, extracts of rocks or stones, enzymes or derivatives thereof, coenzymes or derivatives thereof, for instance coenzyme Q10, hormones or "hormone-like" substances, for instance Phyto age™, soybean extracts, for instance Raffermine™, wheat extracts, for instance Tensine™ or Gliadine™, plant extracts, tannin-rich plant extracts, isoflavone-rich extracts or terpene-rich extracts, freshwater or saltwater algal extracts, marine extracts in general, including coral extracts, essential waxes, bacterial extracts, minerals, for instance the range of Givobio™ products and especially the calcium, magnesium, copper, cobalt, zinc, manganese, etc. derivatives, lipids in general, lipids such as ceramides or phospholipids and also derivatives, active agents with a slimming action, for instance caffeine or its derivatives, active agents that improve the capillary circulation of the skin, for instance venotonic agents, draining active agents, decongestive active agents such as ginko biloba, ivy, common horsechestnut, bamboo, ruscus, centella asiatica, fucus, rosemary or sage, active agents with antimicrobial activity or a purifying action on greasy skin, for instance copper or zinc derivatives or octopirox or Sensiva SC50, active agents with energizing or stimulating properties, for instance Sepitonic™ M3 or Physiogenyl™, panthenol and its derivatives, for instance Sepicap™ MP, anti-ageing active agents, Sepivinol™, Sepivital™, Manoliva™ and Phyto age™. The composition of the invention may also more generally be combined with anti-ageing active agents for combating photoageing, the targeted active agents protecting the integrity of the dermo-epidermal junction, active agents that increase the synthesis of components of the extracellular matrix (for instance collagen, elastins, glycosaminoglycans, etc.), active agents that act favourably on chemical (cytokines) or physical (integrins) cell communication, active agents with a restructuring effect, active agents with a cicatrizing effect, active agents with a firming effect, active agents with a "botox-like" effect, active agents that act on expression wrinkles, active agents that act on the calcium channels, active agents that improve the integrity of the skin barrier, active agents that act on specific skin enzymes, active agents that act on specific cell receptors, active agents that improve cell communication, active agents with a free-radical-scavenging or anti-oxidant effect, active agents with a "tensioning" effect and active agents with an antidandruff, anti-acne, calmative or anti-neuromediator effect. The composition containing the polymer according to the invention may also be combined with active agents that afford a heating effect on the skin, such as skin capillary circulation activators (for example nicotinates) or ingredients that create, conversely, a sensation of freshness on application (for example menthol).

As sunscreens that may be incorporated with the composition of the invention, mention may be made of any of those featured in the amended Cosmetic Directive 76/768/EEC appendix VII.

According to this preferred aspect, the sunscreen is more particularly chosen from lipophilic sunscreens, for instance octocrylene, etocrylene, homosalate, for instance Eusolex™ HMS, octyl para-methoxycinnamate, for instance Parsol™ MCX, octinoxate, octisalate, avobenzone, oxybenzone, benzophenone-1, benzophenone-2, benzophenone-3, for instance Uvinul M-40, benzophenone-8, benzophenone-12, ethyl dihydroxypropyl PABA, glyceryl PABA, ethylhexyl dimethyl PABA, menthyl anthranilate, methylbenzylidenecamphor or isopropyl-dibenzoylmethane.

The sunscreen as defined above may also comprise one or more lipophobic sunscreens, for instance titanium dioxide, zinc oxide, phenylbenzimidazolesulfonic acid, benzophenone-4, TEA salicylate, PABA and DEA methoxycinnamate.

The sunscreen as defined above may also comprise one or more oil absorbers, for instance silica, whether these are spherical silicas, for instance Spheron™ L-1500, porous silica or pyrogenic silica, crosslinked or non-crosslinked polymethyl methacrylate, for instance the Micropearl™ products, dextrins, cyclodextrins, molecular sieves, for instance zeolites, Nylon 6 or 12, sodium calcium aluminosilicate, talc or mica.

The sunscreen as defined above may also comprise one or more esters of neopentanoic acid with an isoalkyl alcohol containing from 10 to 22 carbon atoms. In this case, it preferably comprises isodecyl neopentanoate, isostearyl neopentanoate or isoarachidyl neopentanoate.

According to a particular aspect of the invention, the cosmetic, dermopharmaceutical or pharmaceutical composition comprises an efficient quantity of dihydroxyacetone and more particularly between 1% and 8% by weight of the composition of dihydroxyacetone.

According to a more particular aspect of the invention, the cosmetic, dermopharmaceutical or pharmaceutical composition comprises either dihydroxyacetone and at least a hydroxy acid such as lactic acid, salicylic acid, gluconic acid or kojic acid either dihydroxyacetone and at least one sunscreen agent either dihydroxyacetone and at least one moisterizing agent, either dihydroxyacetone and at least on slimming agent such as caffeine.

BRIEF DESCRIPTION OF THE DRAWINGS

FIG. 1 shows mass concentrations of Triglyceride 5545 prepared according to a first embodiment of the present invention;

FIG. 2 shows mass concentrations of Primol™ 352 prepared according to an embodiment of the present invention; and FIG. 3 shows mass concentrations of Triglyceride 5545 prepared using a conventional emulsion.

The examples that follow are intended to illustrate the present invention without, however, limiting it. They show that the novel inverse lattices do not irritate the skin and that their physical properties allow them to be used in the preparation of cosmetic, dermopharmaceutical or pharmaceutical compositions more particularly intended for treating sensitive skin.

A)—EXAMPLES OF PREPARATION OF COMPOSITIONS ACCORDING TO THE INVENTION

Example 1

Inverse Latex of an (AMPS Na Salt)/DMA Copolymer (90/10), Crosslinked with Methylenebis(acrylamide), in Isohexadecane (Composition 1)

a)—The following are placed in a reactor with stirring:
  17.0 g of deionized water,
  662.1 g of a commercial solution containing 55% sodium 2-methyl-2-[(1-oxo-2-propenyl)amino]-1-propane-sulfonate (AMPS Na salt),
  17.5 g of N,N-dimethylacrylamide (DMA),
  0.45 g of sodium diethylenetriaminepentaacetate,
  0.068 g of methylenebis(acrylamide).
  The pH of this aqueous solution is equal to 5.5.

b)—An organic phase is prepared by mixing together:
  235 g of isohexadecane,
  20 g of sorbitan isostearate (Montane™ 70),
  5 g of Hypermer™ 2296,
  0.058 g of azobis(isobutyronitrile).

c)—The aqueous phase is gradually introduced into the organic phase and the mixture is stirred vigorously using a Silverson™ or IKA™ stirrer, for example. The emulsion obtained is then transferred into a polymerization reactor, sparged with nitrogen and then cooled to about 5-6° C. 250 ml of a solution containing 0.635% by weight of cumene hydroperoxide in isohexadecane is then added, followed, after homogenization of the solution, by addition of an aqueous solution of sodium metabisulfite (0.2% by weight in water) at a rate of 0.2 ml/minute for about 60 minutes, while allowing the temperature to rise to room temperature at the end of polymerization. The reaction medium is then maintained for about 90 minutes at this temperature. 5% of polysorbate 60 (Montanox™ 60) is then added to obtain the desired inverse latex.

Evaluation of the Properties
  Viscosity of the inverse latex at 2% by mass in deionized water
    (Brookfield RVT spindle 6, speed 5): $\eta$=33 400 mPa·s
  Viscosity of the inverse latex at 3% by mass in deionized water+0.1% NaCl
    (Brookfield RVT spindle 6, speed 5): $\eta$=17 200 mPa·s

Example 2

Inverse Latex of an (AMPS Na Salt)/DMA Copolymer (90/10), Crosslinked with Methylenebis(acrylamide), in Isohexadecane (Composition 2)

The experimental conditions of Example 1 are reproduced, but using 0.109 g of methylenebisacrylamide instead of the 0.068 g of the above example. The expected inverse latex is obtained.

Evaluation of the Properties
  Viscosity of the inverse latex at 3% by mass in deionized water
    (Brookfield RVT spindle 6, speed 5): $\eta$=77 400 mPa·s Viscosity of the inverse latex at 3% by mass in deionized water+0.1% NaCl (Brookfield RVT spindle 6, speed 5): η=11 780 mPa·s

Example 3

Inverse Latex of an (AMPS Na Salt)/DMA Copolymer (80/20), Crosslinked with Methylenebis(acrylamide), in Isohexadecane (Composition 3)

The experimental conditions of Example 1 are reproduced, but using 622.9 g of a commercial solution containing 55% sodium 2-methyl-2-[(1-oxo-2-propenyl)amino]-1-propanesulfonate (AMPS Na salt) and 37 g of N,N-dimethylacrylamide (DMA) to obtain a desired (AMPS Na salt)/DMA mole ratio (80/20), and also 0.072 g of methylenebisacrylamide. The expected inverse latex is obtained.

Evaluation of the Properties

Viscosity of the inverse latex at 3% by mass in deionized water (Brookfield RVT spindle 6, speed 5): η=54 800 mPa·s Viscosity of the inverse latex at 3% by mass in deionized water+0.1% NaCl (Brookfield RVT spindle 6, speed 5): η=17 200 mPa·s

Example 4

Inverse Latex of an (AMPS Na Salt)/DMA Copolymer (50/50), Crosslinked with Methylenebis(acrylamide), in Isohexadecane (Composition 4)

The experimental conditions of Example 1 are reproduced, but using 471.6 g of a commercial solution containing 55% sodium 2-methyl-2-[(1-oxo-2-propenyl)amino]-1-propanesulfonate (AMPS Na salt) and 112 g of N,N-dimethylacrylamide (DMA) to obtain the desired (AMPS Na salt)/DMA mole ratio (50/50), and also 0.087 g of methylenebisacrylamide. The expected inverse latex is obtained.

Evaluation of the Properties

Viscosity of the inverse latex at 3% by mass in deionized water (Brookfield RVT spindle 6, speed 5): η=106 000 mPa·s Viscosity of the inverse latex at 3% by mass in deionized water+0.1% NaCl (Brookfield RVT spindle 6, speed 5): η=23 200 mPa·s

Example 5

Inverse Latex of an (AMPS Na Salt)/DMA Copolymer (40/60), Crosslinked with Methylenebis(acrylamide), in Isohexadecane (Composition 5)

The experimental conditions of Example 1 are reproduced, but using 388.6 g of a commercial solution containing 55% sodium 2-methyl-2-[(1-oxo-2-propenyl)amino]-1-propanesulfonate (AMPS Na salt) and 138.6 g of N,N-dimethylacrylamide (DMA) to obtain the desired (AMPS Na salt)/DMA mole ratio (40/60), and also 0.089 g of methylenebisacrylamide. The expected inverse latex is obtained.

Evaluation of the Properties

Viscosity of the inverse latex at 3% by mass in deionized water (Brookfield RVT spindle 6, speed 5): η=89 400 mPa·s Viscosity of the inverse latex at 3% by mass in deionized water+0.1% NaCl (Brookfield RVT spindle 6, speed 5): η=17 820 mPa·s

B)—COMPARISON BETWEEN THE PROPERTIES OF AN INVERSE LATEX ACCORDING TO THE INVENTION AND AN INVERSE LATEX ACCORDING TO THE PRIOR ART

The performance qualities of the inverse latex according to the invention of Example 5 (Composition 5) were compared with those of an inverse latex of an (AMPS Na salt)/acrylamide copolymer (40/60), crosslinked with methylenebis (acrylamide) of the prior art (composition a).

a) Establishment of the Viscosity Curves as a Function of the Concentration of Each of the Inverse Latices Samples are prepared at each of the measured concentrations, by gradually adding the required amount of water to each of the inverse latices.

Their viscosity was measured (Brookfield RVT viscometer spindle 6, speed 5), after leaving them to stand for 7 days at room temperature. The results given in the table below are obtained.

|  | Viscosities (in mpa·s) | |
| --- | --- | --- |
| Concentrations | Composition 5 | Composition (a) |
| 0.5% | 1 300 | 1 200 |
| 1.0% | 20 000 | 18 500 |
| 1.5% | 46 000 | 53 000 |
| 2.0% | 58 000 | 81 000 |
| 2.5% | 77 000 | 92 000 |
| 3.0% | 87 000 | 108 000 |
| 3.5% | 97 000 | 128 000 |
| 4.0% | 100 000 | 134 000 |
| 4.5% | 114 000 | 147 000 |
| 5.0% | 118 000 | 168 000 |

These measurements show similar behaviour in terms of viscosity as a function of the concentration for the two inverse latices.

b) Oil-stabilizing Power of Each of the Inverse Latices

The object of the experiments is to determine the maximum amount of oil that can be incorporated into an aqueous gel of the inverse latex according to the invention of Example 5 (Composition 5).

An aqueous gel of each of the inverse latices having a viscosity of 100 000 mPa·s at room temperature is prepared. Samples of cream-gels are prepared by adding the oil (Primol™ 352 or Triglyceride 5545). The observations are given in the following tables and in FIGS. 1 and 2.

| Mass concentrations of Triglyceride 5545 in the cream-gel prepared with Composition 5 | | | | | | | | |
|---|---|---|---|---|---|---|---|---|
| 30% | 35% | 40% | 45% | 50% | 55% | 60% | 65% | 70% |
| *Appearance and pH of the cream-gel after 1 day* | | | | | | | | |
| compact white 5.4 | compact white 5.4 | compact white 5.4 | compact white 5.5 | compact white 5.6 | compact white 5.6 | compact white 5.6 | compact white 6.7 | compact white 6.2 |
| *Viscosity of the cream-gel after 1 day at room temperature (Brookfield RTV viscometer, spindle 6 speed 5; in Pa·s)* | | | | | | | | |
| 117 | 121 | 125 | 120 | 140 | 140 | 110 | 110 | 145 |
| *Stability of the cream-gel at 40° C. and at 50° C.* | | | | | | | | |
| stable | stable | stable | stable | stable | stable | stable | stable | stable |
| *Appearance and pH of the cream-gel after 7 days* | | | | | | | | |
| compact white 5.3 | compact white 5.4 | compact white 5.5 | compact white 5.7 | compact white 5.6 | compact white 5.8 | compact white 5.8 | compact white 5.7 | compact white 6.2 |
| *Viscosity of the cream-gel after 7 days at room temperature (Brookfield RTV viscometer, spindle 6 speed 5; in Pa·s)* | | | | | | | | |
| 107 | 124 | 120 | 124 | 125 | n.s. | 108–145 | 71–156 | 56–114 |
| *Stability of the cream-gel at 40° C. and at 50° C.* | | | | | | | | |
| stable | stable | stable | stable | stable | stable | stable | stable | stable |
| *Appearance and pH of the cream-gel after 1 month* | | | | | | | | |
| compact white 4.8 | compact white 4.8 | compact white 4.8 | compact white 5.2 | compact white 5.1 | compact white 4.9 | compact white 4.8 | compact white 5.0 | compact white 5.3 |
| *Viscosity of the cream-gel after 1 month at room temperature (Brookfield RTV viscometer, spindle 6 speed 5; in Pa·s)* | | | | | | | | |
| 108 | 119 | 124 | 126 | 127 | 143 | 135 | 92–132 | 143–186 |
| *Stability of the cream-gel at 40° C. and at 50° C.* | | | | | | | | |
| stable | stable | stable | stable | stable | stable | stable | stable | stable |
| *Appearance and pH of the cream-gel after 3 months* | | | | | | | | |
| compact white 4.9 | compact white 4.7 | compact white 4.6 | compact white 4.9 | compact white — | compact white 4.7 | compact white 4.7 | compact white 4.6 | compact white 5.1 |
| *Viscosity of the cream-gel after 3 months at room temperature (Brookfield RTV viscometer, spindle 6 speed 5; in Pa·s)* | | | | | | | | |
| 95 | n.s. | n.s. | n.s. | n.s. | n.s. | n.s. | n.s. | n.s. |
| *Stability of the cream-gel at 40° C. and at 50° C.* | | | | | | | | |
| stable | stable | stable | stable | stable | stable | stable | stable | stable |
| *Appearance and pH of the cream-gel after 6 months* | | | | | | | | |
| compact white 4.4 | compact white 4.4 | compact white 4.3 | compact white n.s. | compact white n.s. | n.s | compact white 4.6 | compact white 5.2 | compact white 4.9 |
| *Viscosity of the cream-gel after 6 months at room temperature (Brookfield RTV viscometer, spindle 6 speed 5; in Pa·s)* | | | | | | | | |
| 110 | 105 | n.s. | n.s. | n.s. | n.s. | 96–183 | n.s. | n.s. |
| *Stability of the cream-gel at 40° C. and at 50° C.* | | | | | | | | |
| stable | stable | stable | stable | stable | stable | stable | stable | stable |

| Mass concentrations of Primol ™ 352 in the cream-gel prepared with Composition 5 | | | | |
|---|---|---|---|---|
| 30% | 40% | 50% | 60% | 70% |
| *Appearance and pH of the cream-gel after 1 day* | | | | |
| compact white 5.0 | compact white 4.9 | compact white 4.8 | compact white 4.9 | compact white 5.0 |

| Viscosity of the cream-gel after 1 day at room temperature (Brookfield RTV viscometer, spindle 6 speed 5; in Pa·s) | | | | |
|---|---|---|---|---|
| 110 | 104 | 122 | 105 | 53–117 |

| Stability of the cream-gel at 40° C. and at 50° C. | | | | |
|---|---|---|---|---|
| stable | stable | stable | stable | stable |

| Appearance and pH of the cream-gel after 7 days | | | | |
|---|---|---|---|---|
| compact white | compact white | compact white | compact white | compact white |
| 4.8 | 4.8 | 5.2 | 4.9 | 4.9 |

| Viscosity of the cream-gel after 7 days at room temperature (Brookfield RTV viscometer, spindle 6 speed 5; in Pa·s) | | | | |
|---|---|---|---|---|
| 91 | 108 | 114 | 105 | n.s. |

| Stability of the cream-gel at 40° C. and at 50° C. | | | | |
|---|---|---|---|---|
| stable | stable | stable | stable | stable |
| compact white | compact white | compact white | compact white | compact white |

| Appearance and pH of the cream-gel after 1 month | | | | |
|---|---|---|---|---|
| 5.3 | 5.2 | 5.2 | 5.5 | 5.3 |

| Viscosity of the cream-gel after 1 month at room temperature (Brookfield RTV viscometer, spindle 6 speed 5; in Pa·s) | | | | |
|---|---|---|---|---|
| 105 | 108 | 111 | 115 | 110 |

| Stability of the cream-gel at 40° C. and at 50° C. | | | | |
|---|---|---|---|---|
| stable | stable | stable | stable | stable |

| Appearance and pH of the cream-gel after 3 months | | | | |
|---|---|---|---|---|
| compact white | compact white | compact white | compact white | compact white |
| 4.2 | 4.3 | 4.3 | 4.7 | 5.8 |

| Viscosity of the cream-gel after 3 months at room temperature (Brookfield RTV viscometer, spindle 6 speed 5; in Pa·s) | | | | |
|---|---|---|---|---|
| 80 | 55 | 41 | 63 | n.s. |

| Stability of the cream-gel at 40° C. and at 50° C. | | | | |
|---|---|---|---|---|
| stable | stable | stable | stable | stable |

| Appearance and pH of the cream-gel after 6 months | | | | |
|---|---|---|---|---|
| compact white | compact white | compact white | compact white | compact white |
| 4.3 | 4.4 | 4.5 | n.s. | n.s. |

| Viscosity of the cream-gel after 6 months at room temperature (Brookfield RTV viscometer, spindle 6 speed 5; in Pa·s) | | | | |
|---|---|---|---|---|
| 72 | 80 | 35 | n.s. | n.s. |

| Stability of the cream-gel at 40° C. and at 50° C. | | | | |
|---|---|---|---|---|
| stable | stable | stable | stable | exudation |

The results demonstrate that Composition 5 makes it possible to emulsify up to 65% of Trigly 5545 (caprylic/capric triglycerides) and up to 60% of Primol™ 352. The same measurements performed on emulsions prepared from inverse latex of an (AMPS Na salt)/acrylamide copolymer (40/60), crosslinked with methylenebis(acrylamide), of the prior art (Composition a), reveal that the maximum amounts emulsified are 45% for Trigly 5545 (see table below and FIG. 3).

| Mass concentrations of Triglyceride 5545 in the cream-gel prepared with Composition a | | |
|---|---|---|
| 40% | 45% | 50% |

| Appearance and pH of the cream-gel after 1 day | | |
|---|---|---|
| compact white | compact white | off-white emulsion |
| 4.7 | 4.7 | |

-continued

| Mass concentrations of Triglyceride 5545 in the cream-gel prepared with Composition a | | |
|---|---|---|
| 40% | 45% | 50% |
| Viscosity of the cream-gel after 1 day at room temperature (Brookfield RTV viscometer, spindle 6 speed 5; in Pa·s) | | |
| 110 | 70 | n.d. |
| Viscosity of the cream-gel after 1 day at 45° C. (Brookfield RTV viscometer, spindle 6 speed 5; in Pa·s) | | |
| 80 | 30 | n.d. |

The same measurements performed on emulsions prepared from inverse latex of an (AMPS Na salt)/acrylamide copolymer (40/60), crosslinked with methylenebis(acrylamide), of the prior art (Composition a), reveal that the maximum amounts emulsified are 40% for Primol™ 352.

It results therefrom that this advantage follows from the substitution in the polymer of the acrylamide monomer with the N,N-dimethylacrylamide monomer.

C)—EXAMPLES OF FORMULATIONS PREPARED WITH THE COMPOSITIONS ACCORDING TO THE INVENTION

Example 6

Care Cream

| | |
|---|---|
| Cyclomethicone: | 10% |
| Inverse latex of Example 1: | 0.8% |
| Montanov ™ 68: | 2% |
| Stearyl alcohol: | 1% |
| Stearyl alcohol: | 0.5% |
| Preserving agent: | 0.65% |
| Lysine: | 0.025% |
| EDTA (disodium salt): | 0.05% |
| Xanthan gum: | 0.2% |
| Glycerol: | 3% |
| Water: | qs 100% |

Example 7

Aftershave Balm

| FORMULA | | |
|---|---|---|
| A | Inverse latex of Example 3: | 1.5% |
| | Water: | qs 100% |
| B | Micropearl ™ M 100: | 5.0% |
| | Sepicide ™ CI: | 0.50% |
| | Fragrance: | 0.20% |
| | 95° ethanol: | 10.0% |

PROCEDURE
Add B to A.

Example 8

Satin Body Emulsion

| FORMULA | | |
|---|---|---|
| A | Simulsol ™ 165: | 5.0% |
| | Lanol ™ 1688: | 8.50% |
| | Shea butter: | 2% |
| | Liquid paraffin: | 6.5% |
| | Lanol ™ 14M: | 3% |
| | Lanol ™ S: | 0.6% |

-continued

| FORMULA | | |
|---|---|---|
| B | Water: | 66.2% |
| C | Micropearl ™ M 100: | 5% |
| D | Inverse latex of Example 5: | 3% |
| E | Sepicide ™ CI: | 0.3% |
| | Sepicide ™ HB: | 0.5% |
| | Aquaxyl ™: | 3% |
| | Fragrance: | 0.20% |
| | Vitamin E acetate: | 0.20% |
| | Sodium pyrolidinonecarboxylate: | 1% |

PROCEDURE
Add C to B, emulsify B in A at 70° C. and then add D at 60° C., followed by E at 30° C.

Example 9

O/W cream

| FORMULA | | |
|---|---|---|
| A | Simulsol ™ 165: | 5.0% |
| | Lanol ™ 1688: | 20.0% |
| | Lanol ™ P: | 1.0% |
| B | Water: | qs 100% |
| C | Inverse latex of Example 2: | 2.50% |
| D | Sepicide ™ CI: | 0.20% |
| | Sepicide ™ HB: | 0.30% |

PROCEDURE
Introduce B into A at about 75° C.; add C at about 60° C., then D at about 45° C.

Example 10

Non-greasy Antisun Gel

| FORMULA | | |
|---|---|---|
| A | Inverse latex of Example 4: | 3.00% |
| | Water: | 30% |
| B | Sepicide ™ CI: | 0.20% |
| | Sepicide ™ HB: | 0.30% |
| | Fragrance: | 0.10% |
| C | Dye: | qs |
| | Water: | 30% |
| D | Micropearl ™ M 100: | 3.00% |
| | Water: | qs 100% |
| E | Silicone oil: | 2.0% |
| | Parsol ™ MCX: | 5.00% |

PROCEDURE
Introduce B into A; add C, then D, then E.

Example 11

Antisun Milk

| FORMULA | | |
|---|---|---|
| A | Montanov ™ S: | 3.0% |
| | Sesame oil: | 5.0% |
| | Parsol ™ MCX: | 5.0% |
| | Carrageenan λ: | 0.10% |

-continued

| | FORMULA | |
|---|---|---|
| B | Water: | qs 100% |
| C | Inverse latex of Example 1: | 0.80% |
| D | Fragrance: | qs |
| | Preserving agent: | qs |

PROCEDURE

Emulsify B in A at 75° C. then add C at about 60° C., followed by D at about 30° C., and adjust the pH if necessary.

Example 12

Massage Gel

| | FORMULA | |
|---|---|---|
| A | Inverse latex of Example 3: | 3.5% |
| | Water: | 20.0% |
| B | Dye: | 2 drops/100 g |
| | Water: | qs |
| C | Alcohol: | 10% |
| | Menthol: | 0.10% |
| D | Silicone oil: | 5.0% |

PROCEDURE

Add B to A, then add C to the mixture, followed by D.

Example 13

Moisturizing and Matting Foundation

| | FORMULA | |
|---|---|---|
| A | Water: | 20.0% |
| | Butylene glycol: | 4.0% |
| | PEG-400: | 4.0% |
| | Pecosil ™ PS100: | 1.0% |
| | NaOH: | qs pH = 9 |
| | Titanium dioxide: | 7.0% |
| | Talc: | 2.0% |
| | Yellow iron oxide: | 0.8% |
| | Red iron oxide: | 0.3% |
| | Black iron oxide: | 0.05% |
| B | Lanol ™ 99: | 8% |
| | Caprylic/capric triglyceride: | 8% |
| | Montanov ™ 202: | 5.00% |
| C | Water: | qs 100% |
| | Micropearl ™ M305: | 2.0% |
| | Tetrasodium EDTA: | 0.05% |
| D | Cyclomethicone: | 4.0% |
| | Xanthan gum: | 0.2% |
| | Inverse latex of Example 5: | 0.8% |
| E | Sepicide ™ HB: | 0.5% |
| | Sepicide ™ CI: | 0.3% |
| | Fragrance: | 0.2% |

PROCEDURE

Prepare mixtures B + D and A + C at 80° C., then mix together and emulsify the whole.

Example 14

Radiance Gel

| | FORMULA | |
|---|---|---|
| A | Inverse latex of Example 5: | 4% |
| | Water: | 30% |
| B | Elastine HPM: | 5.0% |

-continued

| | FORMULA | |
|---|---|---|
| C | Micropearl ™ M 100: | 3% |
| | Water: | 5% |
| D | Sepicide ™ CI: | 0.2% |
| | Sepicide ™ HB: | 0.3% |
| | Fragrance: | 0.06% |
| | Sodium pyrolidinonecarboxylate 50%: | 1% |
| | Water: | qs 100% |

PROCEDURE

Prepare A; add B, then C, then D.

Example 15

Body Milk

| FORMULA | |
|---|---|
| Montanov ™ S: | 3.5% |
| Lanol ™ 37T: | 8.0% |
| Solagum ™ L: | 0.05% |
| Water: | qs 100% |
| Benzophenone-3: | 2.0% |
| Dimethicone 350 cPs: | 0.05% |
| Inverse latex of Example 4: | 0.8% |
| Preserving agent: | 0.2% |
| Fragrance: | 0.4% |

Example 16

Makeup-removing Emulsion with Sweet Almond Oil

| FORMULA | |
|---|---|
| Montanov ™ 68: | 5% |
| Sweet almond oil: | 5% |
| Water: | qs 100% |
| Inverse latex of Example 3: | 0.3% |
| Glycerol: | 5% |
| Preserving agent: | 0.2% |
| Fragrance: | 0.3% |

Example 17

Moisturizing Cream for Greasy Skin

| FORMULA | |
|---|---|
| Montanov ™ 68: | 5% |
| Cetylstearyl octanoate: | 8% |
| Octyl palmitate: | 2% |
| Water: | qs 100% |
| Inverse latex of Example 2: | 0.6% |
| Micropearl ™ M 100: | 3.0% |
| Mucopolysaccharides: | 5% |
| Sepicide ™ HB: | 0.8% |
| Fragrance: | 0.3% |

Example 18

Alcohol-free Soothing Aftershave Balm

| FORMULA | | |
|---|---|---|
| A | Lipacide ™ PVB: | 1.0% |
|   | Lanol ™ 99: | 2.0% |
|   | Sweet almond oil: | 0.5% |
| B | Inverse latex of Example 1: | 3.5% |
| C | Water: | qs 100% |
| D | Fragrance: | 0.4% |
|   | Sepicide ™ HB: | 0.4% |
|   | Sepicide ™ CI: | 0.2% |

Example 19

Cream with AHA for Sensitive Skin

| FORMULA | |
|---|---|
| Mixture of lauryl amino acids: | 0.1% to 5% |
| Magnesium potassium aspartate: | 0.002% to 0.5% |
| Lanol ™ 99: | 2% |
| Montanov ™ 68: | 5.0% |
| Water: | qs 100% |
| Inverse latex of Example 4: | 1.50% |
| Gluconic acid: | 1.50% |
| Triethylamine: | 0.9% |
| Sepicide ™ HB: | 0.3% |
| Sepicide ™ CI: | 0.2% |
| Fragrance: | 0.4% |

Example 20

After-sun Soothing Care

| FORMULA | |
|---|---|
| Mixture of lauryl amino acids: | 0.1% to 5% |
| Magnesium potassium aspartate: | 0.002% to 0.5% |
| Lanol ™ 99: | 10.0% |
| Water: | qs 100% |
| Inverse latex of Example 2: | 2.50% |
| Sepicide ™ HB: | 0.3% |
| Sepicide ™ CI: | 0.2% |
| Fragrance: | 0.4% |
| Dye: | 0.03% |

Example 21

Makeup-removing Milk

| FORMULA | |
|---|---|
| Sepiperl ™ N: | 3% |
| Primol ™ 352: | 8.0% |
| Sweet almond oil: | 2% |
| Water: | qs 100% |
| Inverse latex of Example 5: | 0.8% |
| Preserving agent: | 0.2% |

Example 22

Fluid Emulsion of Alkaline pH

| FORMULA | |
|---|---|
| Marcol ™ 82: | 5.0% |
| NaOH: | 10.0% |
| Water: | qs 100% |
| Inverse latex of Example 1: | 1.5% |

Example 23

Fluid Foundation

| FORMULA | |
|---|---|
| Simulsol ™ 165: | 5.0% |
| Lanol ™ 84D: | 8.0% |
| Lanol ™ 99: | 5.0% |
| Water: | qs 100% |
| Mineral fillers and pigments: | 10.0% |
| Inverse latex of Example 5: | 1.2% |
| Preserving agent: | 0.2% |
| Fragrance: | 0.4% |

Example 24

Antisun Milk

| FORMULA | |
|---|---|
| Sepiperl ™ N: | 3.5% |
| Lanol ™ 37T: | 10.0% |
| Parsol ™ MCX: | 5.0% |
| Eusolex ™ 4360: | 2.0% |
| Water: | qs 100% |
| Inverse latex of Example 1: | 1.8% |
| Preserving agent: | 0.2% |
| Fragrance: | 0.4% |

Example 25

Eye Contour Gel

| FORMULA | |
|---|---|
| Inverse latex of Example 2: | 2.0% |
| Fragrance: | 0.06% |

-continued

| FORMULA | |
|---|---|
| Sodium pyrrolidinonecarboxylate: | 0.2% |
| Dow Corning ™ 245 Fluid: | 2.0% |
| Water: | qs 100% |

Example 26

Leave-in Care Composition

| FORMULA | |
|---|---|
| Inverse latex of Example 3: | 1.5% |
| Fragrance: | qs |
| Preserving agent: | qs |
| Dow Corning ™ X2 8360: | 5.0% |
| Dow Corning ™ Q2 1401: | 15.0% |
| Water: | qs 100% |

Example 27

Slimming Gel

| FORMULA | |
|---|---|
| Inverse latex of Example 4: | 5% |
| Ethanol: | 30% |
| Menthol: | 0.1% |
| Caffeine: | 2.5% |
| Extract of ruscus: | 2% |
| Extract of ivy: | 2% |
| Sepicide ™ HB: | 1% |
| Water: | qs 100% |

Example 28

Ultra-natural Tinted Cream-gel

| | FORMULA | |
|---|---|---|
| A | Water: | 10.0% |
| | Butylene glycol: | 4.0% |
| | PEG-400: | 4.0% |
| | Pecosil ™ PS100: | 1.5% |
| | NaOH: | qs pH = 7 |
| | Titanium dioxide: | 2.0% |
| | Yellow iron oxide: | 0.8% |
| | Red iron oxide: | 0.3% |
| | Black iron oxide: | 0.05% |
| B | Lanol ™ 99: | 4.0% |
| | Caprylic/capric triglyceride: | 4.0% |
| | Sepifeel ™ One: | 1.0% |
| | Inverse latex of Example 5: | 3.0% |
| C | Water: | qs 100% |
| | Micropearl ™ M305: | 2.0% |
| | Tetrasodium EDTA: | 0.05% |
| | Cyclomethicone: | 4.0% |
| D | Sepicide ™ HB: | 0.5% |
| | Sepicide ™ CI: | 0.3% |
| | Fragrance: | 0.2% |

PROCEDURE
Prepare the mixture B + C, then add A and then D.

Example 29

Care for Greasy Skin

| | FORMULA | |
|---|---|---|
| A | Micropearl ™ M310: | 1.0% |
| | Inverse latex of Example 5: | 5.0% |
| | Octyl isononanoate: | 4.0% |
| B | Water: | qs 100% |
| C | Sepicontrol ™ A5: | 4.0% |
| | Fragrance: | 0.1% |
| | Sepicide ™ HB: | 0.3% |
| | Sepicide ™ CI: | 0.2% |
| D | Capigel ™ 98: | 0.5% |
| | Water: | 10% |

Example 30

Cream with AHA

| | FORMULA | |
|---|---|---|
| A | Montanov ™ 68: | 5.0% |
| | Lipacide ™ PVB: | 1.05% |
| | Lanol ™ 99: | 10.0% |
| B | Water: | qs 100% |
| | Gluconic acid: | 1.5% |
| | TEA (triethanolamine): | 0.9% |
| C | Inverse latex of Example 4: | 1.5% |
| D | Fragrance: | 0.4% |
| | Sepicide ™ HB: | 0.2% |
| | Sepicide ™ CI: | 0.4% |

Example 31

Non-greasy Self-tanning Product for the Face and Body

| | FORMULA | |
|---|---|---|
| A | Lanol ™ 2681: | 3.0% |
| | Inverse latex of Example 3: | 2.5% |
| B | Water: | qs 100% |
| | Dihydroxyacetone: | 3.0% |
| C | Fragrance: | 0.2% |
| | Sepicide ™ HB: | 0.8% |
| | NaOH (sodium hydroxide): | qs pH = 5 |

Example 32

Antisun Milk with Monoï de Tahiti

| | FORMULA | |
|---|---|---|
| A | Monoi de Tahiti: | 10% |
| | Lipacide ™ PVB: | 0.5% |
| | Inverse latex of Example 2: | 2.2% |

-continued

| | FORMULA | |
|---|---|---|
| B | Water: | qs 100% |
| C | Fragrance: | 0.1% |
| | Sepicide ™ HB: | 0.3% |
| | Sepicide ™ CI: | 0.1% |
| | Parsol ™ MCX: | 4.0% |

Example 33

Antisun Care Product for the Face

| | FORMULA | |
|---|---|---|
| A | Cyclomethicone and dimethiconol: | 4.0% |
| | Inverse latex of Example 5: | 3.5% |
| B | Water: | qs 100% |
| C | Fragrance: | 0.1% |
| | Sepicide ™ HB: | 0.3% |
| | Sepicide ™ CI: | 0.21% |
| | Parsol ™ MCX: | 5.0% |
| | Titanium mica: | 2.0% |
| | Lactic acid: | qs pH = 6.5 |

Example 34

Self-tanning Emulsion

| | FORMULA | |
|---|---|---|
| A | Lanol ™ 99: | 15% |
| | Montanov ™ 68: | 5.0% |
| | Parsol ™ MCX: | 3.0% |
| B | Water: | qs 100% |
| | Dihydroxyacetone: | 5.0% |
| | Monosodium phosphate: | 0.2% |
| C | Inverse latex of Example 1: | 0.5% |
| D | Fragrance: | 0.3% |
| | Sepicide ™ HB: | 0.8% |
| | NaOH: | qs pH = 5 |

Example 35

Care Cream

| | | |
|---|---|---|
| | Cyclomethicone: | 10% |
| | Inverse latex of Example 2: | 0.8% |
| | Montanov ™ 68: | 4.5% |
| | Preserving agent: | 0.65% |
| | Lysine: | 0.025% |
| | EDTA (disodium salt): | 0.05% |
| | Xanthan gum: | 0.2% |
| | Glycerol: | 3% |
| | Water: | qs 100% |

Example 36

Care Cream

| | | |
|---|---|---|
| | Cyclomethicone: | 10% |
| | Inverse latex of Example 3: | 0.8% |
| | Montanov ™ 68: | 4.5% |
| | Perfluoropolymethyl isopropyl ether: | 0.5% |
| | Preserving agent: | 0.65% |
| | Lysine: | 0.025% |

-continued

| | | |
|---|---|---|
| | EDTA (disodium salt): | 0.05% |
| | Pemulen ™ TR1: | 0.2% |
| | Glycerol: | 3% |
| | Water: | qs 100% |

Example 37

Body Milk

| | FORMULA | |
|---|---|---|
| A | Simulsol ™ 165: | 5.0% |
| | Lanol ™ 1688: | 12.0% |
| | Lanol ™ 14 M: | 2.0% |
| | Cetyl alcohol: | 0.3% |
| | Schercemol ™ OP: | 3% |
| B | Water: | qs 100% |
| C | Inverse latex of Example 4: | 0.35% |
| D | Sepicide ™ CI: | 0.2% |
| | Sepicide ™ HB: | 0.5% |
| | Fragrance: | 0.20% |

PROCEDURE
Emulsify B in A at about 75° C.; add C at about 60° C., followed by D at about 30° C.

Example 38

Massage Care Gel

| | FORMULA | |
|---|---|---|
| A | Inverse latex of Example 5: | 3.00% |
| | Water: | 30% |
| B | Sepicide ™ CI: | 0.20% |
| | Sepicide ™ HB: | 0.30% |
| | Fragrance: | 0.05% |
| C | Dye: | qs |
| | Water: | qs 100% |
| D | Micropearl ™ SQL: | 5.0% |
| | Lanol ™ 1688: | 2% |

PROCEDURE
Prepare A; add B, then C and then D.

Example 39

Body Milk

| | FORMULA | |
|---|---|---|
| A | Sepiperl ™ N: | 3.0% |
| | Glyceryl triheptonate: | 10.0% |
| B | Water: | qs 100% |
| C | Inverse latex of Example 4: | 1.0% |
| D | Fragrance: | qs |
| | Preserving agent: | qs |

PROCEDURE
Melt A at about 75° C. Emulsify B in A at 75° C. then add C at about 60° C., followed by D.

Example 40

Alcohol-free Soothing Aftershave Balm

| FORMULA | |
|---|---|
| Mixture of lauryl amino acids: | 0.1% to 5% |
| Magnesium potassium aspartate: | 0.002% to 0.5% |
| Lanol ™ 99: | 2% |
| Sweet almond oil: | 0.5% |
| Water: | qs 100% |
| Inverse latex of Example 3: | 3% |
| Sepicide ™ HB: | 0.3% |
| Sepicide ™ CI: | 0.2% |
| Fragrance: | 0.4% |

Example 41

Body Milk

| FORMULA | |
|---|---|
| Sepiperl ™ N: | 3.5% |
| Lanol ™ 37T: | 8.0% |
| Solagum ™ L: | 0.05% |
| Water: | qs 100% |
| Benzophenone-3: | 2.0% |
| Dimethicone 350 cPs: | 0.05% |
| Inverse latex of Example 2: | 0.8% |
| Preserving agent: | 0.2% |
| Fragrance: | 0.4% |

Example 42

Alcohol-free Soothing Aftershave Balm

| | FORMULA | |
|---|---|---|
| A | Lipacide ™ PVB: | 1.0% |
| | Lanol ™ 99: | 2.0% |
| | Sweet almond oil: | 0.5% |
| B | Inverse latex of Example 1: | 3.5% |
| C | Water: | qs 100% |
| D | Fragrance: | 0.4% |
| | Sepicide ™ HB: | 0.4% |
| | Sepicide ™ CI: | 0.2% |

Example 43

Refreshing Aftershave Gel

| | FORMULA | |
|---|---|---|
| A | Lipacide ™ PVB: | 0.5% |
| | Lanol ™ 99: | 5.0% |
| | Inverse latex of Example 2: | 2.5% |
| B | Water: | qs 100% |

| | FORMULA | |
|---|---|---|
| C | Micropearl ™ LM: | 0.5% |
| | Fragrance: | 0.2% |
| | Sepicide ™ HB: | 0.3% |
| | Sepicide ™ CI: | 0.2% |

Example 44

Cream with AHAs

| | FORMULA | |
|---|---|---|
| A | Montanov ™ 68: | 5.0% |
| | Lipacide ™ PVB: | 1.05% |
| | Lanol ™ 99: | 10.0% |
| B | Water: | qs 100% |
| | Gluconic acid: | 1.5% |
| | TEA (triethanolamine): | 0.9% |
| C | Inverse latex of Example 3: | 1.5% |
| D | Fragrance: | 0.4% |
| | Sepicide ™ HB: | 0.2% |
| | Sepicide ™ CI: | 0.4% |

Example 45

Gloss Gel

| | |
|---|---|
| Inverse latex of Example 4: | 1.5% |
| Volatile silicone: | 25% |
| Monopropylene glycol: | 25% |
| Demineralized water: | 10% |
| Glycerol: | qs 100% |

Example 46

Slimming Gel

| | |
|---|---|
| Inverse latex of Example 5: | 1.5% |
| Isononyl isononanoate: | 2% |
| Caffeine: | 5% |
| Ethanol: | 40% |
| Micropearl ™ LM: | 2% |
| Demineralized water: | qs 100% |
| Preserving agent, fragrance: | qs |

Example 47

Makeup-removing Milk

| | |
|---|---|
| simulsol ™ 165: | 4% |
| Montanov ™ 202: | 1% |
| Caprylate/caprate triglyceride: | 15% |

-continued

| | |
|---|---|
| Pecosil ™ DCT: | 1% |
| Demineralized water: | qs |
| Capigel ™ 98: | 0.5% |
| Inverse latex of Example 4: | 1% |
| Proteol ™ APL: | 2% |
| Sodium hydroxide: | qs pH = 7 |

Example 48

Restructuring "rinse-off" Cream Mask for Stressed and Embrittled Hair

| FORMULA | |
|---|---|
| Ketrol ™ T: | 0.5% |
| Pecosil ™ SPP50: | 0.75% |
| N-Cocoyl amino acids: | 0.70% |
| Butylene glycol: | 3.0% |
| Inverse latex of Example 1: | 3.0% |
| Montanov ™ 82: | 3.0% |
| Jojoba oil: | 1.0% |
| Lanol ™ P: | 6.0% |
| Amonyl ™ DM: | 1.0% |
| Lanol ™ 99: | 5.0% |
| Sepicide ™ HB: | 0.3% |
| Sepicide ™ CI: | 0.2% |
| Fragrance: | 0.2% |
| Water: | qs 100% |

Example 49

Antisun Cream

| | |
|---|---|
| Simulsol ™ 165: | 3% |
| Montanov ™ 202: | 2% |
| C12–C15 benzoate: | 8% |
| Pecosil ™ PS 100: | 2% |
| Dimethicone: | 2% |
| Cyclomethicone: | 5% |
| Octyl para-methoxycinnamate: | 6% |
| Benzophenone-3: | 4% |
| Titanium oxide: | 8% |
| Xanthan gum: | 0.2% |
| Butylene glycol: | 5% |
| Demineralized water: | qs 100% |
| Inverse latex of Example 5: | 1.5% |
| Preserving agent, fragrance: | qs |

Example 50

Care Gel for Combination Skin

| | |
|---|---|
| Inverse latex of Example 3: | 4% |
| Plant squalane: | 5% |
| Dimethicone: | 1.5% |
| Sepicontrol ™ A5: | 4% |
| Xanthan gum: | 0.3% |
| Water: | qs 100% |
| Preserving agent, fragrance: | qs |

Example 51

Hair Lotion

| FORMULA | |
|---|---|
| Butylene glycol: | 3.0% |
| Inverse latex of Example 4: | 3% |
| Simulsol ™ 1293: | 3.0% |
| Lactic acid: | qs pH = 6 |
| Sepicide ™ HB: | 0.2% |
| Sepicide ™ CI: | 0.3% |
| Fragrance: | 0.3% |
| Water: | qs 100% |

Example 52

Protective and Relaxing Shampoo

| FORMULA | |
|---|---|
| Amonyl ™ 675 SB: | 5.0% |
| 28% sodium lauryl ether sulfate: | 35.0% |
| Inverse latex of Example 3: | 3.0% |
| Sepicide ™ HB: | 0.5% |
| Sepicide ™ CI: | 0.3% |
| Sodium hydroxide: | qs pH = 7.2 |
| Fragrance: | 0.3% |
| Dye (FDC Blue 1/Yellow 5): | qs |
| Water: | qs 100% |

Example 53

"Leave-on" Protective Product; Anti-stress Haircare

| FORMULA | |
|---|---|
| Ketrol ™ T: | 0.5% |
| Mixture of cocoyl amino acids: | 3.0% |
| Butylene glycol: | 5.0% |
| DC 1501: | 5.0% |
| Composition of Example 1: | 4.0% |
| Sepicide ™ HB: | 0.5% |
| Sepicide ™ CI: | 0.3% |
| Fragrance: | 0.3% |
| Water: | qs 100% |

Example 54

Cream with Vitamins

| | |
|---|---|
| Simulsol ™ 165: | 5% |
| Montanov ™ 202: | 1% |
| Caprylic/capric triglycerides: | 20% |
| Vitamin A palmitate: | 0.2% |
| Vitamin E acetate: | 1% |
| Micropearl ™ M305: | 1.5% |
| Inverse latex of Example 2: | 2% |
| Water: | qs 100% |
| Preserving agent, fragrance: | qs |

Example 55

Antisun Gel

| FORMULA | |
|---|---|
| Inverse latex of Example 5: | 3.00% |
| Sepicide ™ CI: | 0.20% |
| Sepicide ™ HB: | 0.30% |
| Fragrance: | 0.10% |
| Dye: | qs |
| Silica: | 3.00% |
| Water: | qs 100% |
| Silicone oil: | 2.0% |
| Benzophenone-3: | 5.00% |

Example 56

Lip Gloss

| FORMULA | |
|---|---|
| Inverse latex of Example 5: | 1.50% |
| Schercemol ™ TISC: | 15.00% |
| Vistanol ™ NPGC: | 15.00% |
| Candurin Paprika: | 0.50% |
| Montanox ™ 80: | 1.00% |
| Antaron ™ V216: | 0.90% |
| Apricot flavouring: | 0.20% |
| Sepicide ™ HB: | 0.50% |
| C Maltidex ™ H16322: | qs 100% |

Example 57

Pressed Powder for Sunny Climate

| FORMULA | |
|---|---|
| Inverse latex of Example 3: | 2.00% |
| Lanol ™ 99: | 12.00% |
| Sepiwhite ™ MSH: | 1.00% |
| Talc: | 33.00% |
| Micropearl ™ M310: | 3.00% |
| Yellow iron oxide: | 0.80% |
| Red iron oxide: | 0.30% |
| Black iron oxide: | 0.05% |
| Mica: | qs 100% |

Example 58

Emulsion for Atopic Skin

| FORMULA | |
|---|---|
| Arlacel ™ P135: | 2.00% |
| Inverse latex of Example 1: | 1.00% |
| Lanol ™ 1688: | 14.00% |
| Primol ™ 352: | 8.00% |
| Glycerol: | 5.00% |
| Water: | qs 100% |
| Magnesium sulfate: | 0.70% |
| Sepicide ™ HB: | 0.30% |
| Sepicide ™ CI: | 0.20% |
| Micropearl ™ M310: | 5.00% |

Example 59

Soothing Antisun Care (Water-in-silicon)

| FORMULA | |
|---|---|
| Inverse latex of Example 4: | 2.00% |
| DC5225C: | 20.00% |
| DC345: | 10.00% |
| Sepicalm ™ VG: | 3.00% |
| Titanium dioxide MT100T: | 5.00% |
| Zinc oxide Z-Cote HP1: | 5.00% |
| Sepicide ™ HB: | 0.30% |
| Fragrance: | 0.05% |
| Sepicide ™ CI: | 0.20% |
| Glycerol: | 5.00% |
| Sodium chloride: | 2.00% |
| Water: | qs 100% |

Example 60

Multi-phase Care

| FORMULA | |
|---|---|
| Inverse latex of Example 5: | 3.00% |
| C12-15 alkylbenzoate: | 25.00% |
| Aquaxyl ™: | 3.00% |
| Sepitonic ™ M3: | 1.00% |
| Sepicide ™ HB: | 0.50% |
| Sepicide ™ CI: | 0.30% |
| Water: | qs 100% |

Example 61

Self-tanning Gel

| | |
|---|---|
| Inverse latex of Example 4: | 5% |
| Ethanol: | 30% |
| Dihydroxyacetone: | 5% |
| Menthol: | 0.1% |
| Caffeine: | 2.5% |
| Extract of ivy: | 2% |
| Sepicide ™ HB: | 1% |
| Water: | qs 100% |

Example 62

Self-tanning Antisun Milk

| | FORMULA | |
|---|---|---|
| A | Sepiperl ™ N: | 3.0% |
| | Glyceryl triheptonate: | 10.0% |
| | Lipacide ™ PVB: | 0.5% |
| | Inverse latex of Example 2: | 2.2% |
| B | Water: | qs 100% |
| | Dihydroxyacetone: | 5.0% |
| C | Fragrance: | 0.1% |
| | Sepicide ™ HB: | 0.3% |
| | Sepicide ™ CI: | 0.1% |
| | Parsol ™ MCX: | 4.0% |

Example 63

Self-tanning Cream with AHAs

| | FORMULA | |
|---|---|---|
| A | Montanov ™ 68: | 5.0% |
| | Lipacide ™ PVB: | 1.05% |
| | Lanol ™ 99: | 10.0% |
| B | Water: | qs 100% |
| | Gluconic acid: | 1.5% |
| | dihydroxyacetone | 3.0% |
| | TEA (triethanolamine): | 0.9% |
| C | Inverse latex of Example 3: | 1.5% |
| D | Fragrance: | 0.4% |
| | Sepicide ™ HB: | 0.2% |
| | Sepicide ™ CI: | 0.4% |

Example 64

Self-tanning Cream with AHA for Sensitive Skin

| FORMULA | |
|---|---|
| Mixture of lauryl amino acids: | 0.1% to 5% |
| Magnesium potassium aspartate: | 0.002% to 0.5% |
| Lanol ™ 99: | 2% |
| Montanov ™ 68: | 5.0% |
| Water: | qs 100% |
| Inverse latex of Example 4: | 1.50% |
| Lactic acid: | 1.50% |
| Dihydroxyacetone: | 3.5% |
| Triethylamine: | 0.9% |
| Sepicide ™ HB: | 0.3% |
| Sepicide ™ CI: | 0.2% |
| Fragrance: | 0.4% |

Example 65

Satin Self-tanning Moisturizing Emulsion

| | FORMULA | |
|---|---|---|
| A | Simulsol ™ 165: | 5.0% |
| | Lanol ™ 1688: | 8.50% |
| | Shea butter: | 2% |
| | Liquid paraffin: | 6.5% |
| | Lanol ™ 14M: | 3% |
| | Lanol ™ S: | 0.6% |

-continued

| | FORMULA | |
|---|---|---|
| B | Water: | 66.2% |
| | Dihydroxyacetone | 3% |
| C | Micropearl ™ M 100: | 5% |
| D | Inverse latex of Example 5: | 3% |
| E | Sepicide ™ CI: | 0.3% |
| | Sepicide ™ HB: | 0.5% |
| | Aquaxyl ™: | 5% |
| | Fragrance: | 0.20% |
| | Vitamin E acetate: | 0.20% |
| | Sodium pyrolidinonecarboxylate: | 1% |

The definitions of the commercial products used in the examples are as follows:

Simulsol™ 1293 is hydrogenated and ethoxylated castor oil, with an ethoxylation index equal to 40, sold by the company SEPPIC.

Capigel™ 98 is a liquid thickener based on acrylate copolymer sold by the company SEPPIC.

Ketrol™ T is xanthan gum sold by the company Kelco.

Lanol™ 99 is isononyl isononanoate sold by the company SEPPIC.

DC1501 is a mixture of cyclopentasiloxane and dimethiconol sold by the company Dow Chemical.

Montanov™ 82 is an emulsifier based on cetearyl alcohol and cocoylglucoside.

Montanov™ 68 (cetearyl glucoside) is a self-emulsifying composition as described in WO 92/06778, sold by the company SEPPIC.

Micropearl™ M 100 is an ultra-fine powder with a very soft feel and a matting action, sold by the company Matsumo.

Sepicide™ CI, imidazolidineurea, is a preserving agent sold by the company SEPPIC.

Pemulen™ TR1 is an acrylic polymer sold by Goodrich.

Simulsol™ 165 is self-emulsifying glyceryl stearate sold by the company SEPPIC.

Lanol™ 1688 is an emollient ester with a non-greasy effect sold by the company SEPPIC.

Lanol™ 14M and Lanol® S are consistency factors sold by the company SEPPIC.

Sepicide™ HB, which is a mixture of phenoxyethanol, methylparaben, ethylparaben, propylparaben and butylparaben, is a preserving agent sold by the company SEPPIC.

Aquaxyl™ is a moisturizer sold by the company SEPPIC.

Schercemol™ OP is an emollient ester with a non-greasy effect.

Lanol™ P is an additive with a stabilizing effect sold by the company SEPPIC.

Parsol™ MCX is octyl para-methoxycinnamate; sold by the company Givaudan.

Sepiperl™ N is a nacreous agent, sold by the company SEPPIC, based on a mixture of alkylpolyglucosides such as those described in WO 95/13863.

Micropearl™ SQL is a mixture of microparticles containing squalane, which is released by the action of massaging; it is sold by the company Matsumo.

Lanol™ 99 is isononyl isononanoate sold by the company SEPPIC.

Lanol™ 37T is glyceryl triheptanoate, sold by the company SEPPIC.

Solagum™ L is a carrageenan sold by the company SEPPIC.

Marcol™ 82 is a liquid paraffin sold by the company Exxon.

Lanol™ 84D is dioctyl malate sold by the company SEPPIC.

Parsol NOX™ is a sunscreen sold by the company Givaudan.

Eusolex™ 4360 is a sunscreen sold by the company Merck.

Dow Corning™ 245 Fluid is cyclomethicone, sold by the company Dow Corning.

Lipacide™ PVB is an acylated wheat protein hydrolysate sold by the company SEPPIC.

Micropearl™ LM is a mixture of squalane, polymethyl methacrylate and menthol, sold by the company SEPPIC.

Sepicontrol™ A5 is a mixture of capryloylglycine, sarcosine and extract of Cinnamon zylanicum, sold by the company SEPPIC, such as those described in international patent application PCT/FR98/01313 filed on 23 Jun. 1998.

Lanol™ 2681 is a coconut caprylate/caprate mixture sold by the company SEPPIC.

Montanov™ 202 is an APG/fatty alcohol composition as described in WO 98/47610, sold by the company SEPPIC.

Proteol™ APL is a foaming surfactant sold by the company SEPPIC.

Schercemol™ TISC is an ester (triisostearyl citrate) sold by the company Scher.

Vistanol™ NPGC is an ester (neopentyl glycol dicaprate) sold by the company Sewa Kasei.

Antaron™ V216 is a synthetic polymer (PVP/hexadecene copolymer) distributed by the company Univar.

C Maltidex™ H16322 is a polyol (maltitol syrup) sold by the company Cerestar.

Sepiwhite™ MSH is a depigmenting active agent (undecylenoyl phenylalanine) sold by the company SEPPIC.

DC 345 is a cyclomethicone sold by the company Dow Corning.

DC 5225C is a mixture of cyclopentasiloxane and dimethiconecopolyol sold by the company Dow Corning.

Sepicalm™ VG is a soothing active agent (sodium palmitoylproline) sold by the company SEPPIC.

MT100VT is a micronized titanium dioxide that has undergone a surface treatment (aluminium hydroxide/stearic acid) distributed by the company Unipex.

Z-Cote HP1 is a micronized zinc oxide that has undergone a surface treatment, distributed by Gattefosse.

Candurin Paprika is a mixture of potassium aluminium silicate and iron oxide.

The invention claimed is:

1. A composition comprising:
an oil phase;
an aqueous phase;
at least one water-in-oil (W/O) emulsifying system;
optionally at least one oil-in-water (O/W) emulsifying system; and
from 20% to 70% by mass of a branched or crosslinked polyelectrolyte, wherein,
the polyelectrolyte is a copolymer of 2-acrylamido-2-methylpropanesulfonic acid partially or totally salified with N,N-dimethylacrylamide and optionally one or more monomers chosen from monomers containing a partially or totally salified weak acid function and/or from neutral monomers other than N,N-dimethylacrylamide,
the polyelectrolyte comprises between 95 mol % and 25 mol % of partially or totally salified 2-methyl-2-[(1-oxo-2-propenyl)amino]-1-propanesulfonic acid monomer and between 5 mol % and 75 mol % of N,N-dimethylacrylamide monomer, and
said composition is an inverse latex.

2. The composition as defined in claim 1, wherein the polyelectrolyte comprises between 90 mol % and 40 mol % of partially or totally salified 2-methyl-2-[(1-oxo-2-propenyl)amino]-1-propanesulfonic acid monomer and between 10 mol % and 60 mol % of N,N-dimethylacrylamide monomer.

3. The composition as defined in claim 1, wherein, the polyelectrolyte is a copolymer of partially or totally salified 2-acrylamido-2-methylpropanesulfonic acid, of N,N-dimethylacrylamide and of one or more monomers chosen from monomers containing a weak acid function and/or neutral monomers other than N,N-dimethylacrylamide, the mole proportion of all of the monomers chosen from the monomers containing a weak acid function and the neutral monomers other than N,N-dimethylacrylamide is greater than 0% and not grater than 30%.

4. The composition as defined in claim 3, wherein, in the polyelectrolyte present, the mole ratio between the N,N-dimethylacrylamide and all of the monomers chosen from the monomers containing a weak acid function and the neutral monomers other than N,N-dimethylacrylamide is at least equal to 1.

5. The composition as defined in claim 1, wherein the composition comprises an oil-in-water (O/W) emulsifying system.

6. The composition as defined in claim 1, wherein the polyelectrolyte is chosen from:
crosslinked copolymers of 2-methyl-2-[(1-oxo-2-propenyl)amino]-1-propanesulfonic acid partially salified in the form of the sodium salt and of N,N-dimethylacrylamide;
crosslinked copolymers of 2-methyl-2-[(1-oxo-2-propenyl)amino]-1-propanesulfonic acid partially salified in the form of the ammonium salt and of N,N-dimethylacrylamide;
crosslinked copolymers of 2-methyl-2-[(1-oxo-2-propenyl)amino]-1-propanesulfonic acid partially salified in the form of the potassium salt and of N,N-dimethylacrylamide;
crosslinked terpolymers of 2-methyl-2-[(1-oxo-2-propenyl)amino]-1-propanesulfonic acid partially salified in the form of the sodium salt, of the potassium salt or of the ammonium salt, of acrylic acid partially salified in the form of the sodium salt, the potassium salt or the ammonium salt and of N,N-dimethylacrylamide;
crosslinked tetrapolymers of 2-methyl-2-[(1-oxo-2-propenyl)amino]-1-propanesulfonic acid partially salified in the form of the sodium salt, the potassium salt or the ammonium salt, of acrylic acid partially salified in the form of the sodium salt, the potassium salt or the ammonium salt, of N,N-dimethylacrylamide and of acrylamide;
crosslinked terpolymers of 2-methyl-2-[(1-oxo-2-propenyl)amino]-1-propanesulfonic acid partially salified in the form of the sodium salt, the potassium salt or the ammonium salt, of N,N-dimethylacrylamide and of acrylamide;
crosslinked terpolymers of 2-methyl-2-[(1-oxo-2-propenyl)amino]-1-propanesulfonic acid partially salified in the form of the sodium salt, the potassium salt or the ammonium salt, of N,N-dimethylacrylamide and of N-isopropylacrylamide;
crosslinked terpolymers of 2-methyl-2-[(1-oxo-2-propenyl)amino]-1-propanesulfonic acid partially salified in the form of the sodium salt, the potassium salt or the ammonium salt, of N,N-dimethylacrylamide and of N-[2-hydroxy-1,1-bis(hydroxymethyl)ethyl]propenamide;
crosslinked tetrapolymers of 2-methyl-2-[(1-oxo-2-propenyl)amino]-1-propanesulfonic acid partially salified in the form of the sodium salt, the potassium salt or the ammonium salt, of acrylic acid partially salified in the form of the sodium salt, the potassium salt or the ammonium salt, of N,N-dimethylacrylamide and of (2-hydroxyethyl)acrylate; and crosslinked terpolymers of 2-methyl-2-[(1-oxo-2-propenyl)amino]-1-propanesulfonic acid partially salified in the form of the sodium salt, the potassium salt or the ammonium salt, of N,N-dimethylacrylamide and of (2-hydroxyethyl)acrylate.

7. A cosmetic, dermopharmaceutical or pharmaceutical composition, comprising as thickening and/or emulsifying compound at least one inverse latex as defined in claim 1.

8. A sunscreen, comprising at least one sunscreen and the inverse latex as defined in claim 1.

9. A self-tanning composition, comprising an efficient quantity of dihydroxyacetone and the inverse latex as defined in claim 1.

10. The cosmetic, dermopharmaceutical or pharmaceutical composition as defined in claim 7, comprising dihydroxyacetone and at least one component selected from the group consisting of lactic acid, gluconic acid, a sunscreen agent, a moisturizing agent, and caffeine.

11. The composition defined in claim 1, wherein the polyelectrolyte is 25% to 50% by mass of said composition.

* * * * *